(12) United States Patent
Mohapatra et al.

(10) Patent No.: US 8,467,868 B1
(45) Date of Patent: Jun. 18, 2013

(54) METHOD OF TRANSDERMAL DRUG DELIVERY

(75) Inventors: Shyam S. Mohapatra, Tampa, FL (US); Arun Kumar, Tampa, FL (US); Bishwabhusan Sahoo, Tampa, FL (US)

(73) Assignee: University of South Florida, Tampa, FL (US)

( * ) Notice: Subject to any disclaimer, the term of this patent is extended or adjusted under 35 U.S.C. 154(b) by 1704 days.

(21) Appl. No.: 11/380,306

(22) Filed: Apr. 26, 2006

Related U.S. Application Data

(60) Provisional application No. 60/674,941, filed on Apr. 26, 2005.

(51) Int. Cl.
*A61N 1/30* (2006.01)
*A61N 1/00* (2006.01)
(52) U.S. Cl.
USPC .............................. 604/20; 607/101; 607/154
(58) Field of Classification Search
USPC ...................................... 604/20; 607/101, 151
See application file for complete search history.

(56) References Cited

U.S. PATENT DOCUMENTS

| 6,148,232 | A | * | 11/2000 | Avrahami | 604/20 |
| 7,415,306 | B2 | * | 8/2008 | Levin et al. | 604/20 |
| 2003/0124175 | A1 | * | 7/2003 | Garavani et al. | 424/449 |
| 2004/0220622 | A1 | | 11/2004 | Bernabei | |
| 2006/0188578 | A1 | * | 8/2006 | Fernandez et al. | 424/489 |

OTHER PUBLICATIONS

Sintov et al., Radiofrequency-driven skin microchanneling as a new way for electrically assisted transdermal delivery of hydrophilic drugs, 2003, Journal of Controlled Release, vol. 89, pp. 311-320.*

* cited by examiner

*Primary Examiner* — Ali Soroush
(74) *Attorney, Agent, or Firm* — Michele L. Lawson; Michael McGaw; Smith & Hopen, P.A.

(57) ABSTRACT

A method of transdermal drug delivery using drug formulations and other small molecules is described. The drug or other small molecule formulation is applied to the skin of a patient using a radio frequency device. The radio frequency device facilitates the ablation of the stratum corneum allowing the drug or other small molecule to pass to the underlying skin. The drug or small molecule can be contained in hyaluronic acid nanoparticles or suspended in a gel.

15 Claims, 4 Drawing Sheets

METHOD OF TRANSDERMAL DRUG DELIVERY

CROSS REFERENCE TO RELATED APPLICATIONS

This application claims priority to currently pending U.S. Provisional Patent Application 60/674,941, entitled, "Method of Transdermal Drug Delivery Using Hyaluronic Acid Nanaparticles", filed Apr. 26, 2005.

FIELD OF INVENTION

This invention relates to transdermal drug delivery. More specifically, this invention relates to transdermal drug and small molecule delivery of formulations using radio frequency-controlled devices.

BACKGROUND OF THE INVENTION

There is considerable interest in the skin as a site of drug application both for local and systemic effect. However, the skin, and in particular the stratum corneum, poses a formidable barrier to drug and other small molecule penetration thereby limiting topical and transdermal bioavailability. Skin penetration enhancement techniques have been developed to improve bioavailability and increase the range of drugs for which topical and transdermal delivery is a viable option. Enhancement techniques have focused on drug/vehicle optimization such as drug selection, prodrugs and ion-pairs, supersaturated drug solutions, eutectic systems, complexation, liposomes, vesicles and particles. Enhancement via modification of the stratum corneum by hydration, chemical enhancers acting on the structure of the stratum corneum lipids and keratin, partitioning and solubility effects have also been investigated as important parameters for optimization.

A number of drugs and other small molecules may be administered transdermally. Transdermal drug absorption can significantly alter drug kinetics. Transdermal drug absorption depends on a variety of factors including the site of application, thickness and integrity of the stratum corneum epidermidis, size of the molecule, permeability of the membrane of the transdermal drug delivery system, state of skin hydration, pH of the drug, drug metabolism by skin flora, lipid solubility, depot of drug in skin, and alteration of blood flow in the skin by additives and body temperature. The potential for toxic effects of the drug and difficulty in limiting drug uptake are major considerations for nearly all transdermal delivery systems. This is especially true in children because skin thickness and blood flow in the skin vary with age. The relatively rich blood supply in the skin combined with thinner skin has significant effects on the pharmacokinetics of transdermal delivery systems for children. In some situations this may be an advantage, while in others systemic toxicity may result. For example, central nervous system toxicity has been observed in neonates washed with hexachlorophene. The toxicity occurred due to the very thin skin and large body surface area of the neonates, allowing toxic levels to develop from systemic drug absorption.

Transdermal delivery of drugs and other small molecules has been investigated extensively. Some benefits of transdermal drug delivery include the enhancement of the therapeutic effect of the drugs, while minimizing side effects for topical and systemic drug delivery. In topical applications, drugs are delivered to the site of interest with a specific drug concentration. Drugs can also be administrated systemically without hepatic first pass metabolism and dose levels can be stabilized. Most drugs show limited absorption through the skin, because the stratum corneum (SC), the outermost layer of the skin, works as an effective barrier to molecular transport. The SC is composed of corneocytes (dead cells) which are filled with keratin. The intercellular regions within the SC are mainly occupied by neutral lipids. In general, there are three possible pathways for transdermal drug delivery: transport through appendages such as hair follicles, transcellular transport through the corneocytes, and intercellular transport via the extra cellular matrix. In addition to vehicle formulations and chemical enhancers, various physical methods have been investigated so far for transdermal drug delivery. These methods include continuous electric current (iontophoresis), electric pulses (electroporation) and ultrasound (phonophoresis, sonophoresis). These physical methods have an advantage associated with the excellent temporal controllability of drug release. Transdermal drug delivery by laser-induced stress waves (LISWs) has been reported. The LISWs generated by high-power pulsed lasers are characterized by broadband, unipolar and compressive waves. The LISWs interact with tissues in ways that are different from those of ultrasound. The action of ultrasound is primarily mediated by heat and cavitation induced by a negative pressure. The effects of the LISWs are caused by positive mechanical forces. It has been shown in vivo that a single LISW can increase the permeability of the SC. Currently the mechanism of permeabilization of the SC by applying a LISW is not well understood.

The transdermal patch has become a proven technology that offers a variety of significant clinical benefits over other dosage forms. Transdermal drug delivery offers the controlled release of the drug into the patient. This enables a steady blood-level profile, resulting in reduced systemic side effects and, sometimes, improved efficacy over other dosage forms. In addition, because transdermal patches are user-friendly, convenient, painless, and offer multi-day dosing, it is generally accepted that they offer improved patient compliance. Transdermal patch formulation is an area of continued interest. Because drug-in-adhesive technology has become the preferred system for passive transdermal delivery, two areas of formulation research are focused on adhesives and excipients. Adhesive research focuses on customizing the adhesive to improve skin adhesion over the wear period, improve drug stability and solubility, reduce lag time, and increase the rate of delivery. Because a one-size-fits-all adhesive does not exist that can accommodate all drug and formulation chemistries, customizing the adhesive chemistry allows the transdermal formulator to optimize the performance of the transdermal patch.

SUMMARY OF INVENTION

A method of transdermal drug delivery of drug formulations and other small molecules is described. The drug formulation or small molecule is applied to the skin of a patient using a radio frequency device. The radio frequency device facilitates the ablation of the stratum corneum allowing the drug or small molecules to pass to the underlying skin. The drug or small molecule can be contained in a nanoparticle or suspended in a gel. The nanoparticle can be a hyaluronic acid nanoparticle.

In accordance with the present invention there is provided a method for the transdermal delivery of a drug formulation or other small molecule to a patient using a radio frequency (RF) treatment including the steps of providing a drug or other small molecule and applying the drug formulation or other small molecule to the skin of a patient using a radio frequency device. The radiofrequency device ablates the stratum corneum to facilitate passage of the drug or other small molecule to the underlying layer of the skin. The radio frequency treatment can provide microchannels of about 100 microns or less in the stratum corneum of the patient to facilitate delivery of the drug formulation or other small molecule into the skin of a patient. In specific embodiments the drug or other small molecule is in a nanoparticle. The nanoparticle can be made of hyaluronic acid. The drug or other small molecule can alternatively be suspended in a gel. The gel can be a mixture of beeswax, rice bran oil and glycerol. In certain embodiments the radio frequency device can include a formulation dispenser for holding the drug or other small molecule, an applicator membrane in contact with the formulation dispenser, wherein the applicator membrane has pores to enable the passage of the drug or other small molecule from the RF device to the skin of a patient, and a radio frequency device in contact with the formulation dispenser, wherein activation of the radio frequency device ablates the skin of a patient and facilitates the flow of the drug or other small molecule from the formulation dispenser to the patient's skin.

In certain embodiments the present invention provides a device for treating a patient by applying a substance to a patient's skin. The device includes a formulation dispenser for holding the drug or other small molecule, an applicator membrane in contact with the formulation dispenser, wherein the applicator membrane has pores to enable the passage of the drug or other small molecule from the RF device to the skin of a patient and a radio frequency device in contact with the formulation dispenser, wherein activation of the radio frequency device ablates the skin of a patient and facilitates the flow of the drug or other small molecule from the formulation dispenser to the patient's skin.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
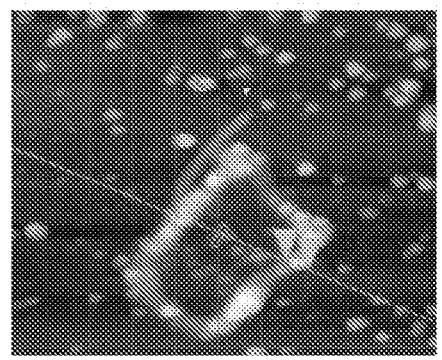
FIG. 1 is a series of photographs showing the synthesis and characterization of nanochitosan particles produced by proprietary methods. (A) Atomic force microscopic analysis of Nanogene-042 particles showing oligomeric structure complexed with DNA (dark arrowhead in upper center of photograph). (B) Nanogene-031 nanoparticles given intranasally to mice to deliver genes to both the proximal and distal lung, as shown using the gene for green fluorescent protein (arrow). (C) BALB/c mice were given pSV40-GFP plasmid (25 μg/mouse, intranasally in nanoparticles). Mice were imaged 24 h later using the In Vivo Imaging System (IVIS-100, Xenogen, CA). The results show that the luciferase-expressing tumor cells can be detected using this method. Also, Imaging of GFP expression in the lung and other tissues can be accomplished using Fluorescent imaging through the Xenogen Imaging system.
Figure 1B:
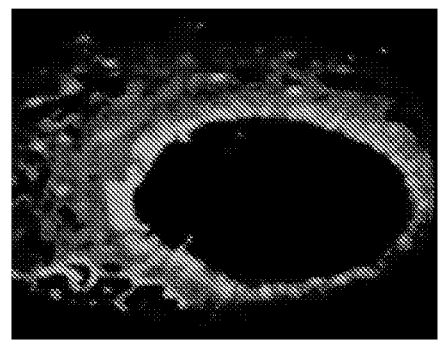
Figure 1C:
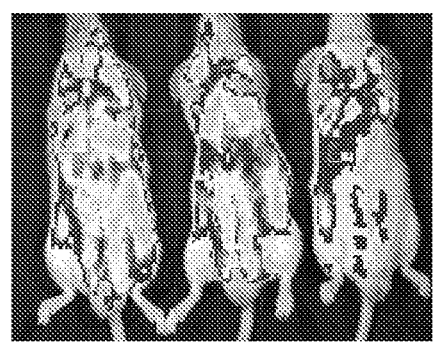

This invention pertains to the development of a novel method of transdermal drug delivery that involves delivery of drug formulations and other small molecules which are administered using a non-invasive radio frequency (RF)-controlled device. The RF device is placed over the formulation dispenser. The formulation dispenser includes a container connector attached to the flexible container and an applicator having a sealed piercing member with the container connector. An porous applicator membrane has enlarged holes for passage of the drugs or other small molecules in gel or liquid formulation. The gel formulation dispenser pierces a seal in the container and delivers the gel/liquid formulation from the container to the application site only with RF device. Flow rate of the drug or other small molecule gel formulation is controlled by the optimized RF frequency.

Local inflammation and inability to deliver various drugs are some of the major problems with current transdermal drug delivery systems. RF devices have been of considerable interest in using non-ablative methods to rejuvenate the skin Radiofrequency (RF) devices have been used to induce tightening of the skin via a uniform volumetric heating into the deep dermis. The technique was found to produce gradual tightening in most cases, and there were no adverse effects.

Delivery of drugs or other small molecules transdermally may be improved by temporarily increasing the skin pore sizes with controlled application of heat. As proof of concept, first drug/small molecule delivery was tested using nanoparticles of hyaluronic acid. These nanoparticles can be delivered through the transdermal means using a non-ablative RF device, which is expected to improve all skin conditions including laxity, wrinkles, clarity, and pore size. Complications and side effects were minimal. Low cost and portability are some of the benefits of the system. In addition, the system is easy to use and can be used for various drugs.

The invention will be further described by way of the following non-limiting examples.

EXAMPLE 1

Development and Characterization of Nanochitsan Particles

Water soluble low molecular weight chitosan is produced by cleaving the main chains with acidic hydrolysis, enzymatic degradation and irradiation [Ono K, Ishihara M, Ozeki Y, Deguchi H, Sato M, Saito Y, Yura H, Sato M, Kikuchi M, Kurita A, Maehara T. Surgery. 2001 November; 130(5):844-50]. Water soluble low molecular weight chitosan has some advantages, such as higher biocompatibility, solubility in neutral water and organic solvents, and ease of chemical modification. Four chitosan-based polymers in the range of 1-10 KDa, referred to as nanochitosan, have been identified in our laboratory using a proprietary method. They include NG031, NG042 and NG044. NG031 is a polymeric complex of chitosan, lipid and DNA, which provides increased efficiency for gene transfer and safety, making it specifically useful for DNA vaccines. NG042 is a carrier that was identified as a potential drug carrier based on its size (avg. size of 150 nm) and zeta potential of 20 mV. A decrease in particle size and an increase in hydrophobicity have been attributed to the increased antibody responses for influenza whole or split vaccine, bovine serum albumin and HIV split virus. NG044 was recently identified to have thermogelling properties, forming a gel at 37° C. and above but remaining a liquid solution at room temperature. The products thus obtained were dialyzed against water. The supernatant containing oligomers were passed through a charcoal-Celite column and desalted using Sephadex G15. Fractions containing reducing groups were pooled and freeze dried. The molecular mass was measured by capillary electrophoresis, viscometric measurements, gel permeation chromatography and HPLC. Each of the major components was produced in sufficient quantity by gel exclusion chromatography for further characterization. Fractions with potential will be further characterized for size, zeta potential, water solubility, thermostabilty and thermogelling properties, using standard methods.

EXAMPLE 2

Development and Characterization of Hyaluronic Acid Nanoparticles

Figure 2A:
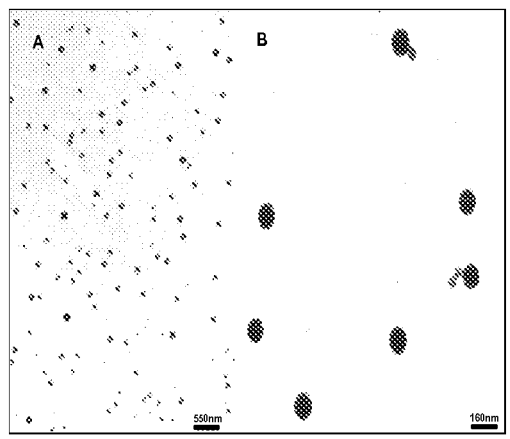
FIG. 2 illustrates the modification of HA nanoparticles. (A) TEM of modified HA nanoparticles. TEM of HA nanoparticle (left) 18,000× and (right) 62,000× magnification. (B) IR spectra of modified HA nanoparticles. IR spectra of HA (upper) and of HA nanoparticle crosslinked with dihydrazide (lower). The lower panel shows that the amide I and amide II band at 1676 and 1601 $cm^{-1}$ is enhanced as compared to starting HA, indicating crosslinking reaction. Also, the peak at 1272 and 1359, which correspond to the C—N/C—O and $CH_2$ stretch indicate presence of the pendant hydrazide group. (C) $^1H$ NMR spectra of modified HA nanoparticles. The $^1H$ NMR spectra were measured in $D_2O$ solutions using a VARIAN UNITY 400 spectrometer operating at frequencies of 400 MHz. No standard TMS were used for this measurement. Samples were kept in Wilmad 5 mm NMR tubes in $D_2O$ for 4 hrs prior to experiment. The NMR spectra were accumulated at 27° C. Upper panel corresponds to the proton NMR spectra of HA (64 scan) and lower panel shows the NMR spectra of HA nanoparticle (512 scan) crosslinked with dihydrazide. The region at 3.0-3.8 ppm shows clearly from both the spectra as the sugar —CH— protons from HA. The extra peak at 2.75 and 2.67 are due to the —$CH_2$—NH— from the hydrazide. The noise intensity is higher in case of HA-particle than the HA itself suggesting the cross linking. Also, increase of noise is due to suspended particles in water.
Figure 2B:
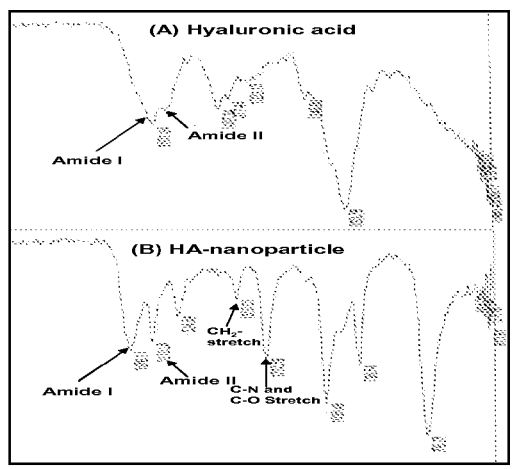
Figure 2C:
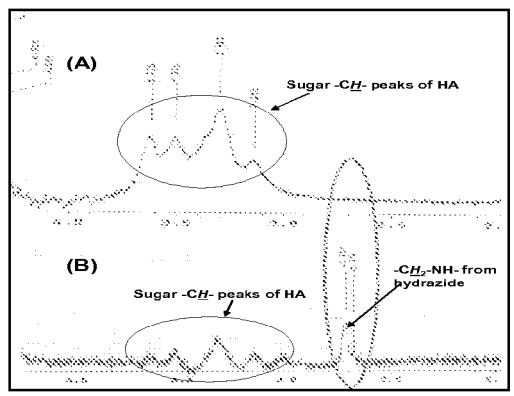

The nanoparticles were prepared by self-assembling micro-emulsions techniques and were encapsulated using surfactants. Briefly, functionalized HA (Sigma) and a dihydrazide were mixed, homogenized and incubated with a crosslinking reagent in an aqueous solution. The aqueous solution was added to a non-polar organic solvent and a biodegradable surfactant to form an oil-in-water type emulsion. The pH of the reaction was lowered to pH 4.0 to allow intermolecular and intermolecular crosslinking reaction and subsequent formation of nanospheres. In preliminary studies, the HA nanoparticles were characterized by transmission electron microscope (TEM), NMR, FT-IR and atomic force microscope. As shown in FIG. 2 A-B, a TEM analysis of the HA nanoparticle complexed with FITC, gives the particle size of diameter ranging from 80-160 nm. Analysis by FT-IR confirmed cross linking reaction between the HA polymers and the outer surface containing the hydrazide pendant group. NMR analysis indicated crosslinking and modification of HA.

To examine potential of HA nanoparticles in peptide and gene transfer, experiments were conducted using human embryonic kidney (HEK293) epithelial cells. First, HEK293 cells were incubated with nanoparticles of HA encapsulating ANP peptide linked with FITC and the cells were examined under fluorescence microscope at 24, 48 and 72 h after incubation. The results showed that almost all cells were capable of taking in these particles (FIG. 3A). Also, HEK293 cells were transfected with HA nanoparticles encapsulating plasmid DNA, which encodes DS-Red protein. The results showed that the cells were capable of taking in nanoparticle carried DNA (FIG. 3B).

EXAMPLE 3

Demonstration of Peptide and DNA Delivery of HA Nanoparticles

Figure 3:
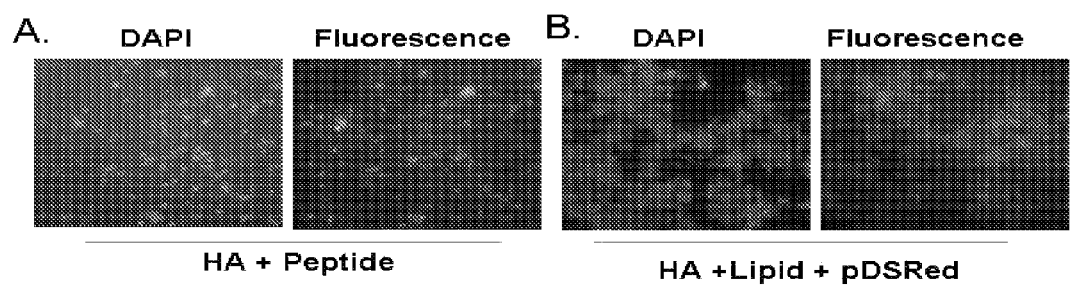
FIG. 3 is a series of photographs demonstrating peptide and DNA delivery of HA nanoparticles.
Figure 4:
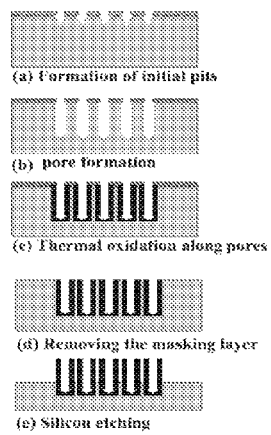
FIG. 4 is a schematic representation of the formation of silica nanopores.

FIG. 3 shows photographs of HEK293 cells that were incubated with HA nanoparticles encapsulating either NP-73-102 peptide-labeled with FITC (3A) or plasmid encoding pDS-Red (3B). Cells were observed under fluorescence microscope after 72 h. Cells were stained with nuclear stain DAPI to show the presence of live cells (See FIG. 3).

EXAMPLE 4

Fabrications of RF Device for Transdermal Drug Delivery

Figure 5:
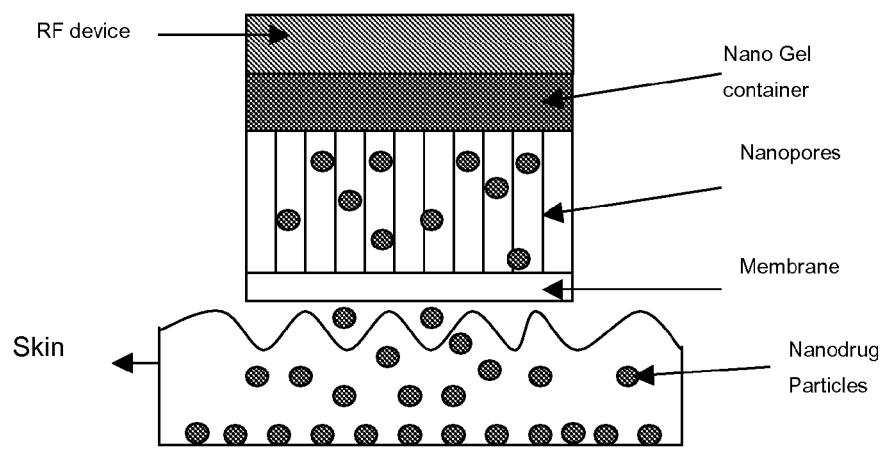
FIG. 5 is a schematic representation of a radio frequency dispenser of a gel.

The RF device was placed over the gel formulation dispenser. The gel formulation dispenser includes a container connector connected to the flexible container and a gel applicator having a sealed piercing member which is slidably engaged with the container connector (FIG. 5). An applicator membrane is porous having enlarged holes for passage of the gel formulation. The gel formulation dispenser pierces a seal in the container and delivers the antimalarial alcohol gel formulation from the container to the application site only with RF device. Flow rate of the gel formulation is controlled by the optimized RF frequency.

EXAMPLE 5

Formulation of Nanoparticles Gel

In a typical formulation, take the Beewax and melt it at 60-70° C. Add 2 times the Rice Bran oil to it and stir it at 200 rpm for 30 mins at 60° C. Allow it to cool to 30° C. It will form an oily substance. Add hyaluronic acid nanoparticle encapsulated with premaquine diphosphate and stir vigorously at 800-1000 rpm till it get thick. Add propelyne glycol (1:30 w/w) and again stir it for 30 mins. Ensure that the mixture is homogenous and that no air remains. Then add little glycerol to make more thin paste.

Working Mechanism of Radiofrequency (RF) Ablation:

Electromagnetic radiation is characterized by a broad range of wavelengths and frequencies, each associated with a specific intensity (or amplitude) and quantity of energy. Electromagnetic radiation (RF), energy radiated in the form of a wave as a result of the motion of electric charges_Goldberg S N, Solbiati L, Halpern E F, Gazelle G S. *J Vasc Interv Radiol.* 2000 September; 11(8):1069-75. A moving charge gives rise to a magnetic field, and if the motion is changing (accelerated), then the magnetic field varies and in turn produces an electric field. A high-frequency electromagnetic wave is emitted from an RF (radio frequency) device which is basically a low-cost unit.

The RF device enables the insertion of the drug into skin. Through the liquid coupling medium the RF device creates cavitation bubbles that expand and contract in the coupling medium. RF device disorganizes the lipid bi-layer of the stratum corneum, creating reversible micro-channels in the skin through which fluids and nanoparticles can be inserted and large molecules can also be delivered. Narins D J, Narins R S. *J Drugs Dermatol.* 2003 October; 2(5):495-500. RF signals involve remarkable amounts of energy in the form of mechanical pressure change, movements or torque forces, temperature change etc. This energy is used to stimulate the skin surface cells for transdermal diffusion of drug. Experiments have clearly demonstrated the ability of RF energy to warm hands and feet in cold environments. Lloyd J R, Olsen R G. *Undersea Biomed Res.* 1992 May; 19(3):199-207.

Figure 6:
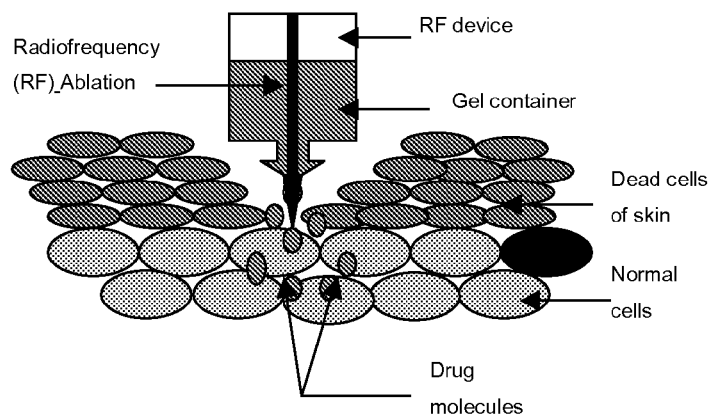
FIG. 6 is a schematic representation of the mechanism of radiofrequency ablation.

The following steps are involved in the mechanism (as outlined in FIG. 6)

Step 1. RF device delivery drug inside the chamber and energy released from RF waves change of pressure inside the chamber the dissolved gases expand and contract which causes cavitations.

Step 2. Radio frequency ablation alters the structure of lipid bilayer of the stratum corneum washing away fats and oils, holding away the skin intact and removing the dead cells of the skin.

Step 3. The RF treatment creates reversible micro channels about 100 micron or less smaller then the standard hair through which gel can be delivered without the use of needle and skin returns to normal in few minutes.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the transdermal delivery of a drug formulation to a patient using a radio frequency (RF) treatment comprising the steps of:
   providing a drug encapsulated within a nanoparticle; and
   applying radio frequency energy to the skin of a patient to create reversible microchannels that facilitate passage of the drug through the skin; wherein applying the radio frequency energy is performed by a device comprising: a power source emitting radio energy; a drug dispenser in contact with the power source; and a porous applicator membrane in contact with the drug dispenser; whereby the activation of the power source emits radio frequency energy and ablates the skin of a patient and facilitates the flow of the drug from the device through the skin of a patient.

2. The method according to claim 1 wherein the microchannels are about 100 microns or less through the stratum corneum of the patient.

3. The method according to claim 1 wherein the drug is encapsulated within a hyaluronic acid nanoparticle.

4. The method according to claim 1 wherein the nanoparticle-encapsulated drug is suspended in a gel.

5. The method according to claim 4 wherein the gel comprises beeswax, rice bran oil and glycerol.

6. The method of claim 1 wherein the nanoparticle-encapsulated drug is suspended in a liquid.

7. A device for the transdermal delivery of a drug to a patient comprising:
   a power source capable of emitting radio frequency energy;
   a drug dispenser in contact with the power source; and
   a porous applicator membrane in contact with the drug dispenser;
   whereby the activation of the power source emits radio frequency energy and ablates the skin of a patient and facilitates the flow of the drug from the device through the skin of a patient.

8. The device of claim 7 wherein the drug is suspended in a liquid or gel.

9. The method of claim 7 wherein the drug is encapsulated in a nanoparticle.

10. The method of claim 9 wherein the nanoparticle is a hyaluronic acid nanoparticle.

11. A method for the transdermal delivery of a drug to a patient using a radio frequency (RF) treatment comprising the steps of:
    providing a drug encapsulated within a hyaluronic acid nanoparticle; and
    applying radio frequency energy to the skin of a patient to create reversible microchannels that facilitate passage of the small molecule through the skin.

12. The method according to claim 11 wherein the microchannels are about 100 microns or less through the stratum corneum of the patient.

13. The method according to claim 11 wherein the nanoparticle-encapsulated drug is suspended in a gel.

14. The method according to claim 13 wherein the gel comprises beeswax, rice bran oil and glycerol.

15. The method of claim 11 wherein the nanoparticle-encapsulated drug is suspended in a liquid.

\* \* \* \* \*